United States Patent
Liang et al.

(10) Patent No.: US 6,462,236 B2
(45) Date of Patent: Oct. 8, 2002

(54) PREPARATION OF AMINES

(75) Inventors: Shelue Liang, Ludwigshafen; Frank Funke, Frankenthal; Arthur Höhn, Kirchheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/983,307

(22) Filed: Oct. 24, 2001

(65) Prior Publication Data

US 2002/0082455 A1 Jun. 27, 2002

(30) Foreign Application Priority Data

Oct. 27, 2000 (DE) .......................... 100 53 380

(51) Int. Cl.⁷ ...................... C07C 209/26; C07C 209/16
(52) U.S. Cl. ................ 564/336; 564/397; 564/398
(58) Field of Search ................ 564/366, 397, 564/398

(56) References Cited

U.S. PATENT DOCUMENTS 5,011,996 A   4/1991   Kiel et al.

FOREIGN PATENT DOCUMENTS

EP    355 351    2/1990
GB    969 977    9/1964

OTHER PUBLICATIONS

Houben–Weyl) Methoden Der Organischen Chemie Band IV/1c; 1980, pp. 436–437.

*Primary Examiner*—Brian J. Davis
(74) *Attorney, Agent, or Firm*—Keil & Weinkauf

(57) ABSTRACT

Amines of the formula (I)

$$R^1R^2CH-NR^3R^4 \quad (I)$$

where $R^1$, $R^2$, $R^3$ and $R^4$ are each, independently of one another, hydrogen, straight-chain or branched $C_1-C_{12}$-alkyl, $C_3-C_{12}$-cycloalkyl, $C_6-C_{10}$-aryl or $C_7-C_{11}$-aralkyl, where at least one of the radicals $R^1$ and $R^2$ is aryl or aralkyl whose aromatic unit is substituted by at least one halogen, are prepared by catalytic, hydrogenative amination of carbonyl compounds of the formula (II) or alcohols of the formula (III)

$$R^1-C(=O)-R^2 \quad (II)$$

$$R^1-CH(OH)-R^2 \quad (III)$$

by means of nitrogen compounds of the formula (IV)

$$HNR^3R^4 \quad (IV)$$

where $R^1$ to $R^4$ are as defined above, in the presence of Co- and/or Ni-containing catalysts, in the additional presence of solid acid cocatalysts and in the absence of organic sulfur compounds.

10 Claims, No Drawings

PREPARATION OF AMINES

The present invention relates to a process for preparing amines by catalytic hydrogenative amination of carbonyl compounds or alcohols having at least one halogen-substituted aromatic unit which is not changed in the hydrogenative amination.

The hydrogenative amination of carbonyl compounds by means of ammonia or primary or secondary amines is a standard method of preparing amines. The reaction is customarily carried out in the presence of metallic catalysts, for example Raney Ni, Raney Co, Pt/activated carbon, Pd/activated carbon, Pd/BaSO$_4$, Rh/Al$_2$O$_3$. In Houben-Weyl, Methoden der Organischen Chemie, 4th edition, volume IV/Ic, Reduction part I, Thieme Verlag, 1980, pages 436 and 437, it is stated that chlorine bound to an aromatic ring is not attacked in the hydrogenative amination using Raney nickel. Two reactions are reported by way of example, but these lead to low yields. Dehalogenation presumably occured as a significant secondary reaction in the examples given.

GB 969,977 describes substituted 1,3-diphenylpropylamine and corresponding imines. Example 6 describes the hydrogenative amination of 1-(2-ethyl-4,5-dimethoxyphenyl)-3-(4-chlorophenyl)-1-propenol by means of ammonia over Raney nickel as catalyst. After work-up, 1-amino-1-(2-ethyl-4,5-dimethoxyphenyl)-3-(chlorophenyl)propane hydrochloride is obtained as product.

EP-A-0 355 351 relates to a process for preparing amines by reductive amination of oxo compounds containing halogen-substituted aromatic substituents. The reaction is, in particular, carried out over Raney Ni or Raney Co in the presence of ammonia or amines. In addition, the reaction is carried out in the presence of organic sulfur compounds such as dimethyl sulfoxide or bis(2-hydroxyethyl) sulfide. The organic sulfur compound is used in an amount of preferably from 1 to 25% by weight, based on the catalyst. Relative to the carbonyl compound, amounts of more than 1% by weight are present. The sulfur compounds serve to partially poison the catalyst, so that the halogen bound to the aromatic ring can be retained. For example, the amination of p-chloroacetophenone gives yields of p-chlorophenylethylamine of up to 90% under suitable conditions.

However, the addition of relatively large amounts of sulfur compounds is disadvantageous since it introduces a further component into the reaction system and this can make work-up of the reaction products, in particular by distillation, more difficult. In addition, the organic sulfur compounds result in increased catalyst consumption, typically over 6% by weight of the Ni catalyst, based on the carbonyl compound used.

It is an object of the present invention to provide a process for preparing amines having at least one halogen-substituted aromatic unit by hydrogenative amination of corresponding carbonyl compounds or alcohols with retention of the halogen-substituted aromatic units, which process avoids the disadvantages of the known processes and leads to the desired products in high yields using small amounts of catalyst.

We have found that this object is achieved by a process for preparing amines of the formula (I)

$$R^1R^2CH\text{—}NR^3R^4 \quad (I)$$

where $R^1$, $R^2$, $R^3$ and $R^4$ are each, independently of one another, hydrogen, straight-chain or branched $C_1$–$C_{12}$-alkyl, $C_3$–$C_{12}$-cycloalkyl, $C_6$–$C_{10}$-aryl or $C_7$–$C_{11}$-aralkyl, where at least one of the radicals $R_1$ and $R^2$ is aryl or aralkyl whose aromatic unit is substituted by at least one halogen, by catalytic, hydrogenative amination of carbonyl compounds of the formula (II) or alcohols of the formula (III)

$$R^1\text{—}C(=O)\text{—}R^2 \quad (II)$$

$$R^1\text{—}CH(OH)\text{—}R^2 \quad (III)$$

by means of nitrogen compounds of the formula (IV)

$$HNR^3R^4 \quad (IV)$$

where $R^1$ to $R^4$ are as defined above, in the presence of Co- and/or Ni-containing catalysts, in the additional presence of solid acid cocatalysts and in the absence of organic sulfur compounds.

According to the present invention, it has been found that very good amine yields can be achieved in the hydrogenative amination of haloaryl ketones, aldehydes or alcohols with substantial retention of the halogen bound to the aromatic ring even without addition of organic sulfur compounds if the Co- and/or Ni-containing catalysts employed in the reaction are used in combination with solid acid cocatalysts.

The Co- and/or Ni-containing catalysts are preferably selected from among Raney Co, Raney Ni, Raney Co—Ni, Raney Ni—Fe, Raney Ni—Fe—Co, nickel oxides, cobalt oxides, mixed Ni/Co oxides and mixtures thereof, which may also be present on inorganic supports.

The Co and/or Ni catalysts may further comprise from 0 to 80% by weight of Cu and from 0 to 10% by weight, preferably from 0 to 5% by weight, of other metals, calculated as metal and based on the total weight of the catalyst.

In the process of the present invention, the Co- and/or Ni-containing catalysts are preferably used in the form of elemental Co and/or Ni sponge, Raney cobalt or Raney nickel, Co or Ni or cobalt oxide or nickel oxide on supports (supported catalysts). They can also be used as mixtures in any mixing ratios. Examples of supports for these catalysts are Al$_2$O$_3$, SiO$_2$, TiO$_2$, ZrO$_2$, activated carbon and other catalyst supports known to those skilled in the art.

Among the Raney catalysts, preference is given to using Raney catalysts such as Raney cobalt, Raney cobalt-nickel, Raney cobalt-nickel-iron, Raney cobalt-nickel-iron-chromium or Raney cobalt or Raney nickel containing other transition metals as dopants in dry form, moist with water or moist with solvent. Particular preference is given to using Raney cobalt containing either 0 or from 0.1 to 10% by weight, preferably up to 5% by weight, of Al, Ni, Fe, Cr. The Co- or Ni-containing catalyst is used in an amount of from 0.01 to 20% by weight, preferably from 0.1 to 10% by weight and particularly preferably from 0.3 to 5% by weight, based on the carbonyl compound to be aminated.

According to the present invention, preference is also given to using a Co—Ni catalyst which is supported on ZrO$_2$ and contains from 0 to 50% by weight of CuO, and calculated as CuO and based on the total weight of the catalyst.

The solid acid cocatalysts are, according to the present invention, preferably selected from among metal oxides and mixed metal oxides, zeolites, metal salts and ammonium salts of mineral acids and organic acids, acid ion exchangers and mixtures thereof.

As solid acid cocatalysts in the process of the present invention, preference is given to using metal oxides such as oxides or mixed oxides of the elements Zr, Ti, Cr, Mo, W, Mn, Fe, B, Al, Si, zeolites of natural or synthetic origin, metal salts or ammonium salts of strong mineral acids such as hydrochloric acid, sulfuric acid, nitric acid, phosphoric acid and strong organic acids such as formic acid, acetic acid, propionic acid and sulfonic acids, acid ion exchangers such as Nafion, etc. The amounts of the acid cocatalysts used are preferably in the range from 0.1 to 20% by weight, preferably 1–10% by weight, based on the carbonyl compound to be aminated.

When using supported Co- or Ni-containing catalysts, the support materials such as $Al_2O_3$, $SiO_2$, $TiO_2$, $ZrO_2$, etc., can function as acid cocatalysts. In this case, the addition of an additional acid cocatalyst is unnecessary. If ammonium salts are used as acid cocatalysts, the corresponding acid can be used directly instead of the ammonium salt. The ammonium salts are then formed by reaction of the acid with ammonia or amines.

In the process of the present invention, the acid cocatalysts used are preferably metal oxides or mixtures thereof. Particular preference is given to $ZrO_2$.

The carbonyl compounds or alcohols used according to the present invention may be chosen essentially without restriction. They have at least one aryl or aralkyl radical whose aromatic unit is substituted by at least one halogen atom. It is preferably substituted by chlorine in particular by one chlorine atom.

The aryl radicals are particularly preferably phenyl radicals and the aralkyl radicals are particularly preferably benzyl radicals. The alkyl radicals are preferably $C_{1-6}$-alkyl radicals, and the cycloalkyl radicals are preferably $C_{3-6}$-cycloalkyl radicals. In the compounds of the formulae (II) and (III), it is particularly preferred that none of the radicals is hydrogen. In particular, $R_1$ is phenyl substituted by one chlorine atom and $R^2$ is $C_{1-6}$-alkyl. Particular preference is given to using p-chloroacetophenone as carbonyl compound. The nitrogen compound of the formula (IV) is preferably ammonia or a primary or secondary aliphatic amine. The latter preferably bears $C_{1-6}$-alkyl radicals. Particular preference is given to using ammonia as nitrogen compound.

The amination in the process of the present invention can be carried out in solvents, for example alcohols such as methanol, ethanol, propanol, butanol, aliphatic or aromatic hydrocarbons such as toluene, xylene, cyclohexane, isooctane, ethers such as tetrahydrofuran, dioxane, methyl tert-butyl ether. However, in a preferred embodiment, no additional solvent is used, but instead the aminating agent used in excess (ammonia or amines) simultaneously functions as solvent. The molar ratio of ammonia or amine to carbonyl compound is preferably greater than 1, for rapid reactions preferably greater than 2.

The amination is preferably carried out at from 10 to 250° C., preferably from 40 to 150° C., and at a pressure of from 10 to 200 bar, preferably from 30 to 130 bar.

The process of the present invention can be carried out in a fixed bed, but may also, for example, be carried out in an autoclave. The Co- or Ni-containing catalysts and the acid cocatalysts and also the carbonyl compound are introduced under protective gas into the reactor in any order. At room temperature, ammonia or amines are introduced while stirring. The mixture is heated to the reaction temperature, and hydrogen is subsequently injected until the reaction pressure has been reached. After hydrogen uptake has ceased, the reactor is cooled to room temperature, vented and emptied.

The catalysts are filtered off and reused for the next reaction cycle. The work-up of the reaction product is then carried out in a manner known to those skilled in the art.

The process can be carried out either batchwise, for example in an autoclave, or continuously, for example in a pressure tube with attached separator and depressurization.

The use of Co- and Ni-containing catalysts in combination with acid cocatalysts largely suppresses dechlorination in the hydrogenative amination of haloaryl ketones and aldehydes, thus enabling high amine yields to be achieved. The high amine selectivities and yields in the process of the present invention, combined with a simple procedure for the synthesis and omission of organic solvents, make possible a simple work-up and thus overall an economical production process.

The process of the present invention is illustrated by the following examples using p-chloroacetophenone as representative carbonyl compound.

EXAMPLES

The p-chloroacetophenone used in the examples has a purity of >99% (according to GC).

The catalysts used are likewise commercial products having the following compositions:

| | |
|---|---|
| Ra-Co: | Raney cobalt, suspension catalyst |
| Ra-Ni: | Raney nickel, suspension catalyst |
| $Al_2O_3$: | Powder |
| $ZrO_2$: | Powder |
| $TiO_2$: | Powder |
| Al-Si: | Aluminum silicate, powder |
| Ni-Cu | $NiO/CuO/MoO_3/ZrO_2$ (weight ratio-50.6:16.7:1.5:31.2), reduced and partially passivated, milled, powder |
| Ni-Co: | $NiO/CoO/CuO/ZrO_2$ (weight ratio = 28:28:13:31), reduced and partially passivated, milled, powder |

The amination experiments were carried out using the general method described below and are not optimized. Higher amine selectivities and yields might therefore be achievable.

General Method:

The catalysts, p-chloroacetophenone and possibly methanol as solvent are placed in a 2.5 l autoclave which is fitted with a disk stirrer and two baffles and has been flushed and filled with nitrogen. At room temperature, first the ammonia and then the hydrogen are injected to a pressure of 20 bar while stirring (500 revolutions per minute). The mixture is heated to the reaction temperature, further hydrogen is injected until the reaction pressure is reached and the mixture is subsequently stirred under a constant hydrogen pressure. After uptake of hydrogen has ceased, the autoclave is cooled, depressurized, vented and emptied. The compositions of the reaction products are determined by gas chromatography. The experimental results are shown in Table 1.

TABLE 1

Results of the amination of p-chloroacetophenone (CAP)

| Ex. | Catalysts (g) | $CAP/NH_3/MeOH$ [g] | T/P [° C./bar] | Conv. [%] | Amine [%] | Alk.[a] [%] | SB[b] [%] | Dechl.[c] [%] |
|---|---|---|---|---|---|---|---|---|
| 1 | Ra—Co(10)/$Al_2O_3$(30) | 155/850/0 | 50/100 | 100 | 83.7 | 10.4 | 0 | 5.7 |
| 2 | Ra—Co(10)/Al—Si(30) | 155/850/0 | 50/100 | 99.3 | 68.0 | 27.0 | 0 | 2.7 |
| 3 | Ra—Co(5)/$TiO_2$(30) | 155/850/0 | 50/100 | 100 | 66.3 | 29.3 | 0 | 4.2 |
| 4 | Ra—Co(5)/$ZrO_2$(30) | 155/850/0 | 50/100 | 100 | 64.1 | 31.7 | 0 | 3.0 |
| 5 | Ra—Co(2.5)/$ZrO_2$(30) | 155/850/0 | 50/100 | 99.5 | 95.7 | 0 | 1.2 | 1.9 |

TABLE 1-continued

Results of the amination of p-chloroacetophenone (CAP)

| Ex. | Catalysts (g) | CAP/NH$_3$/MeOH [g] | T/P [°C./bar] | Conv. [%] | Amine [%] | Alk.[a] [%] | SB[b] [%] | Dechl.[c] [%] |
|---|---|---|---|---|---|---|---|---|
| 6 | Ra—Co(2.5)/ZrO$_2$(30) | 155/850/0 | 100/100 | 100 | 98.5 | 0.3 | 0 | 1.0 |
| 7 | Ra—Co(2.5)/ZrO$_2$(30) | 310/170/0 | 90/80 | 99.6 | 95.7 | 0.5 | 1.6 | 1.1 |
| 8 | Ra—Co(2.5)/ZrO$_2$(30) | 310/170/170 | 90/80 | 97.3 | 86.4 | 0.7 | 8.7 | 0.8 |
| 9 | Ra—Co(2.5)/TiO$_2$(30) | 310/170/0 | 90/80 | 74.1 | 25.0 | 0.2 | 45.7 | 0.2 |
| 10 | Ra—Ni(2.5)/ZrO$_2$(30) | 310/170/0 | 90/100 | 54.0 | 2.8 | 0.2 | 36.7 | 0.3 |
| 11 | Ra—Ni(2.5)/TiO$_2$(30) | 310/170/0 | 90/100 | 61.6 | 3.2 | 0.1 | 47.3 | 0.4 |
| 12 | Ra—Ni(2.5)/Al—Si(30) | 310/170/0 | 90/80 | 75.7 | 12.3 | 0.1 | 59.4 | 0.1 |
| 13 | Ni—Co(30) | 310/170/0 | 100/80 | 99.2 | 81.2 | 5.7 | 1.2 | 9.6 |
| 14 | Ni—Co(15) | 310/170/0 | 100/80 | 95.1 | 70.8 | 2.2 | 18.0 | 1.7 |
| 15 | Ni—Cu(30) | 310/170/0 | 100/80 | 97.5 | 82.8 | 1.5 | 7.7 | 3.1 |
| 16 | Ni—Cu(16) | 320/408/400 | 120/60 | 100 | 95.3 | 0.5 | 0.3 | 3.2 |

[a]Alk. = 1-(4'-chlorophenyl)ethanol;
[b]SB = Schiff base derived from p-chloroacetophenone and p-chlorophenylethylamine;
[c]Dechl. = sum of the dechlorination products such as phenylethylamine and 1-phenylethanol.

We claim:

1. A process for preparing amines of the formula (I)

$$R^1R^2CH{-}NR^3R^4 \qquad (I)$$

where $R^1$, $R^2$, $R^3$ and $R^4$ are each, independently of one another, hydrogen, straight-chain or branched $C_1$–$C_{12}$-alkyl, $C_3$–$C_{12}$-cycloalkyl, $C_6$–$C_{10}$-aryl or $C_7$–$C_{11}$-aralkyl, where at least one of the radicals $R^1$ and $R^2$ is aryl or aralkyl whose aromatic unit is substituted by at least one halogen, by catalytic, hydrogenative amination of carbonyl compounds of the formula (II) or alcohols of the formula (III)

$$R^1{-}C(={\rm O}){-}R^2 \qquad (II)$$

$$R^1{-}CH(OH){-}R^2 \qquad (III)$$

by means of nitrogen compounds of the formula (IV)

$$HNR^3R^4 \qquad (IV)$$

where $R^1$ to $R^4$ are as defined above, in the presence of Co- and/or Ni-containing catalysts, in the additional presence of solid acid cocatalysts and in the absence of organic sulfur compounds.

2. A process as claimed in claim 1, wherein the solid acid cocatalysts are selected from among metal oxides and mixed metal oxides, zeolites, metal salts and ammonium salts of mineral acids and organic acids, acid ion exchangers and mixtures thereof.

3. A process as claimed in claim 1, wherein the Co- and/or Ni-containing catalysts are selected from among Raney Co, Raney Ni, Raney Ni—Fe, Raney Ni—Fe—Co, nickel oxides, cobalt oxides, mixed Ni/Co oxides and mixtures thereof, which may also be present on inorganic supports.

4. A process as claimed in claim 1, wherein the Co- and/or Ni-containing catalysts further comprise from 0 to 80% by weight of Cu and from 0 to 10% by weight of other metals, calculated as metal and based on the total weight of the catalyst.

5. A process as claimed in claim 4, wherein a Raney Co catalyst which further comprises from 0 to 10% by weight of Al, Ni, Cr and/or Fe, calculated as metal and based on the total weight of the catalyst, is used.

6. A process as claimed in claim 4, wherein a Co—Ni catalyst which is supported on $ZrO_2$ and contains from 0 to 50% by weight of CuO, calculated as CuO and based on the total weight of the catalyst, is used.

7. A process as claimed in claim 1, wherein the solid acid cocatalysts used are oxides and mixed oxides of the elements Zr, Ti, Cr, Mo, W, Mn, Fe, B, Al, Si or mixtures thereof, zeolites, metal salts or ammonium salts of hydrochloric acid, sulfuric acid, nitric acid, phosphoric acid or formic acid, acetic acid, propionic acid or sulfonic acids or acid ion exchangers.

8. A process as claimed in claim 1, wherein the catalysts and cocatalysts are used in suspension.

9. A process as claimed in claim 1, wherein, in the carbonyl compounds of the formula (II) and the alcohols of the formula (III), $R^1$ is phenyl substituted by one chlorine atom and $R^2$ is $C_{1-6}$-alkyl.

10. A process as claimed in claim 9, wherein p-chloroacetophenone is used as carbonyl compound and ammonia is used as nitrogen compound.

* * * * *